United States Patent [19]

Butter et al.

[11] 3,972,832

[45] Aug. 3, 1976

[54] PHOSPHORUS-CONTAINING ZEOLITE CATALYST

[75] Inventors: Stephen A. Butter, East Windsor; Warren W. Kaeding, Westfield, both of N.J.

[73] Assignee: Mobil Oil Corporation, New York, N.Y.

[22] Filed: Sept. 23, 1974

[21] Appl. No.: 508,308

[52] U.S. Cl. ............................ 252/437; 252/455 Z; 260/683.15 C
[51] Int. Cl.² ..................... B01J 27/14; B01J 29/06
[58] Field of Search ..................... 252/437, 455 Z; 260/683.15 C

[56] References Cited
UNITED STATES PATENTS

| | | | |
|---|---|---|---|
| 3,354,096 | 11/1967 | Young | 252/437 X |
| 3,355,246 | 11/1967 | Kuehl | 252/437 X |
| 3,804,746 | 4/1974 | Chu | 252/455 Z |

*Primary Examiner*—Carl F. Dees
*Attorney, Agent, or Firm*—Charles A. Huggett; Raymond W. Barclay

[57] ABSTRACT

This specification discloses, as a composition of matter, a phosphorus-containing zeolite and discloses a method for preparing it. The composition is a crystalline aluminosilicate zeolite having a silica to alumina ratio of at least about 12, a constraint index of about 1 to 12, and containing phosphorus incorporated with the crystal structure thereof in an amount of at least about 0.78 percent by weight. The specification also discloses the use of the composition as a catalyst for the conversion of aliphatic compounds.

32 Claims, No Drawings

3,972,832

PHOSPHORUS-CONTAINING ZEOLITE CATALYST

BACKGROUND OF THE INVENTION

1. Field of the Invention

This invention relates to a phosphorus-containing zeolite and its use as a catalyst for the conversion of aliphatic compounds.

2. Description of the Prior Art

U.S. Pat. No. 3,702,886, issued Nov. 14, 1972, to Argauer et al., discloses ZSM-5 zeolite catalyst.

U.S. Pat. No. 3,709,979, issued Jan. 9, 1971, to Chu, discloses ZSM-11 zeolite catalyst.

West German Offenlagunschrifft No. 2,213,109, published Sept. 21, 1972, to Mobile Oil Corporation, discloses ZSM-12 zeolite catalyst.

Copending application Ser. No. 358,192, filed May 7, 1973, now abandoned and refiled as application Ser. No. 560,412, filed Mar. 20, 1975 discloses ZSM-21 zeolite catalyst.

Copending application Ser. No. 130,442, filed Apr. 11, 1971, now abandoned and refiled as application Ser. No. 500,805, filed Aug. 26, 1974 discloses TEA mordenite.

Copending application Ser. No. 508,307, filed Sept. 23, 1974, discloses the conversion of alcohols or ethers, i.e., methanol or dimethyl ether, to higher carbon number hydrocarbons by contact with a catalyst comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight.

Copending application Ser. No. 508,306, filed Sept. 23, 1974, now U.S. Pat. No. 3,906,054 discloses a process for the alkylation of olefins employing, as a catalyst, a crystalline aluminosilicate zeolite having a silica to alumina ratio of at least about 12, a constraint index of about 1 to 12, and containing phosphorus incorporated with the crystal structure thereof in an amount of at least about 0.78 percent by weight.

U.S. Pat. No. 3,140,249, issued July 7, 1964, to Plank et al., discloses the cracking of hydrocarbons with a crystalline aluminosilicate zeolite catalyst.

SUMMARY OF THE INVENTION

In accordance with a feature of the invention, there is provided, as a composition of matter, a phosphorus-containing zeolite comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight. The amount of the phosphorus incorporated with the crystal structure of the zeolite may be as high as about 4.5 percent by weight and even higher. In accordance with another feature of the invention, the composition of matter is prepared by contacting a crystalline aluminosilicate zeolite containing hydrogen ions and having a silica to alumina ratio of at least about 12 and a constraint index of about 1 to 12 with a phosphorus-containing compound and thereafter heating. In accordance with still another feature of the invention, this composition is employed as a catalyst for the conversion of aliphatic compounds, particularly aliphatic hydrocarbons.

DESCRIPTION OF THE PREFERRED EMBODIMENTS

A group of crystalline aluminosilicate zeolites having a silica to alumina ratio of at least about 12 and a constraint index of about 1 to 12 has recently been discovered to have some very unusual catalytic properties. They induce profound transformations of aliphatic hydrocarbons to aromatic hydrocarbons in commercially desirable yields. Further, although they have unusually low alumina contents, i.e., high silica to alumina ratios, they are active even when the silica to alumina ratio exceeds 30. This activity is considered to be surprising since the alumina in the zeolite framework is believed responsible for catalytic activity. They retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity.

An important characteristic of the crystal structure of these zeolites is that it provides constrained access to, and egress from, the intracrystalline free space by virtue of having a pore dimension greater than about 5 Angstroms and pore windows of about a size such as would be provided by ten-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the center of the tetrahedra. Briefly, the zeolites useful for preparing the phosphorus-containing zeolite of this invention, hereinafter termed "the phosphorus-containing zeolite," possess, in combination, a silica to alumina ratio of at least about 12 and a structure providing constrained access to the crystalline free space defined in terms of a constraint index of about 1 to 12. Further reference will be made hereinafter to the constraint index.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolites with a silica to alumina ratio of at least about 12 are useful to prepare the phosphorus-containing zeolite of this invention, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous.

The zeolites useful for preparation of the phosphorus-containing zeolite of this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight-membered rings of oxygen atoms, then access to molecules of larger cross-section than normal hexane is excluded and the zeolite is not of the desired type. Windows of ten-membered rings are preferred, although excessive puckering or pore blockage may render these zeolites ineffective. Twelve-membered rings do not generally appear to offer sufficient constraint, although structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10 percent and 60 percent. The mixture of hydrocarbons is passed at 1 liquid hourly space velocity (i.e., 1 volume of hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for use are those having a constraint index, as mentioned, from about 1 to 12. Preferably, the constraint index is from about 2 to 7.

The zeolites defined herein are exemplified, to the extent that they have a silica to alumina ratio of at least about 12 and a constraint index of about 1 to 12, by ZSM-5, ZSM-11, ZSM-12, ZSM-21, TEA mordenite and other similar materials.

The entire contents of recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in West German Offenlagunschrifft No. 2,213,109, the entire contents of which are incorporated herein by reference. ZSM-21 is more particularly described in U.S. application Ser. No. 358,192, filed May 7, 1973, the entire contents of which are incorporated herein by reference.

TEA mordenite is more particularly described in U.S. application Ser. No. 130,442, filed Apr. 11, 1971, the entire contents of which are incorporated herein by reference.

The zeolites, when prepared in the presence of organic cations, are catalytically inactive, possibly because the intracrystalline free space is occupied by organic cations from the forming solution. They may be activated by heating in an inert atmosphere at 500° C for one hour, for example, followed by base exchange with ammonium salts followed by calcination at 500° C solution air. The presence of organic cations in the forming solutions may not be absolutely essential to the formation of the zeolite; however, the presence of these cations does appear to favor the formation of these special zeolites. More generally, it is desirable to activate the zeolite by base exchange with ammonium salts followed by calcination in air of about 500° C for from about 15 minutes to about 24 hours.

Natural zeolites may sometimes be converted to zeolites suitable for use in the present invention by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred zeolites are ZSM-5, ZSM-11, ZSM-12, ZSM-21, and TEA mordenite, with ZSM-5 particularly preferred.

In a preferred aspect, the zeolites for preparation of the phosphorus-containing zeolite of this invention are those having a crystal density, in the dry hydrogen form, of not substantially below about 1.6 grams per cubic centimeter. It has been found that zeolites which satisfy all three of these criteria are most desired. Therefore, the preferred phosphorus-containing zeolites are prepared from zeolites having a constraint index as defined above of about 1 to 12, a silica to alumina ratio of at least about 12, and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. This density of not substantially below about 1.6 grams per cubic centimeter of course must be associated with a relatively small amount of free space within the crystal, which might be expected to result in more stable structures. This free space, however, is important as the locus of catalytic activity.

The zeolites whether having phosphorus incorporated therewith or not are capable of having at least a portion of the original cations associated therewith replaced by a wide variety of other cations according to techniques well known in the art. Replacing cations include ammonium and metal cations, including mixtures of the same. The phosphorus-containing zeolite of this invention is prepared from zeolites wherein at least a portion of the original cations associated therewith have been replaced by hydrogen.

The crystalline aluminosilicate zeolites can be converted to the hydrogen form, i.e., having at least a portion of the original cations associated therewith replaced by hydrogen, generally by two methods. The first involves direct ion exchange employing an acid. Suitable acids include both inorganic acids and organic acids. Typical inorganic acids which can be employed include hydrochloric acid, hypochlorous acid, sulfuric acid, sulfurous acid, hydrosulfuric acid, nitric acid, nitrous acid, hyponitrous acid, phosphoric acid, and carbonic acid. Typical organic acids which can be employed are the monocarboxylic and polycarboxylic acids which can be aliphatic, aromatic, or cycloaliphatic in nature. Representative suitable acids include acetic, trichloroacetic, bromoacetic, citric, maleic, fumaric, itaconic, phenylacetic, benzene sulfonic and methane sulfonic acids. The second method for preparing the hydrogen form, which is preferred, involves first preparing an ammonium or other hydrogen ion precursor form by base exchange and then calcining to cause evolution of the ammonia leaving a hydrogen ion remaining on the zeolite. Calcining is carried out in air at 500° C for about 15 minutes to about 24 hours. Suitable compounds for preparing the hydrogen ion precursor form include ammonium compounds such as chloride, bromide, iodide, bicarbonate, sulfate, citrate, borate, and palmitate. Still other ammonium compounds which can be employed include quaternary ammonium compounds such as tetramethylammonium hydroxide and trimethylammonium chloride.

In accordance with a particular aspect of the invention, the phosphorus-containing zeolite of the invention is prepared by reacting a zeolite as defined herein with a phosphorus-containing compound. This may be phosphorus per se or a compound thereof having a covalent or ionic constituent capable of reacting or exchanging with hydrogen ion and thereafter heating.

Any phosphorus-containing compound having a covalent or ionic constituent capable of reacting with hydrogen ion may be employed. Suitable phosphorus-containing compounds include derivatives of groups represented by $PX_3$, $RPX_2$, $R_2PX$, $R_3P$, $R_3P=O$, $RPO_2$, $RP(O)(OX)_2$, $R_2P(O)OX$, $RP(OX)_2$, $ROP(OX)_2$, and $(RO)_2POP(OR)_2$, where R is an alkyl or phenyl radical and X is hydrogen, R, or halide. These compounds include primary, $RPH_2$, secondary, $R_2PH$, and tertiary, $R_3P$, phosphines such as butyl phosphine; the tertiary phosphine oxides, $R_3PO$, such as tributylphosphine oxide; the primary, $RP(O)(OX)_2$, and secondary, $R_2P(O)OX$, phosphonic acids such as benzene phosphonic acid; the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Examples of phosphite esters include trimethylphosphite, triethylphosphite, diisopropylphosphite, butylphosphite; and pyrophosphites such as tetraethylpyrophosphate. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphinochloridites, $R_2PCl$, alkyl alkylphosphonochloridates, $(RO)(R)P(O)Cl$, and dialkyl phosphinochloridates, $R_2P(O)Cl$.

Preferred phosphorus-containing compounds include trimethylphosphite and phosphorus trichloride. In the trimethylphosphite, the covalent ionic constituent capable of reacting with hydrogen ion is $[CH_3-O-]^-$. In the phosphorus trichloride, the covalent or ionic constituent capable of reacting with hydrogen ion is $[-Cl]^-$.

While we do not wish to be limited by the consequences of a theory, it is believed that the constituent of the phosphorus-containing compound capable of reacting with hydrogen ion reacts with the hydrogen of the original zeolite. Thus, with trimethylphosphite, it is believed that the hydrogen on the zeolite reacts with one of the $[CH_3-O-]^-$ ions of the trimethylphosphite to form $CH_3OH$ and is believed thereby to chemically bond the remainder of the trimethylphosphite molecule, namely, the

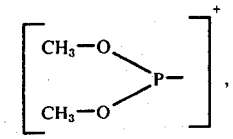

to the crystal structure of the zeolite possibly through a silanol group. In a similar manner, a phosphonate may undergo prototropic change in the manner

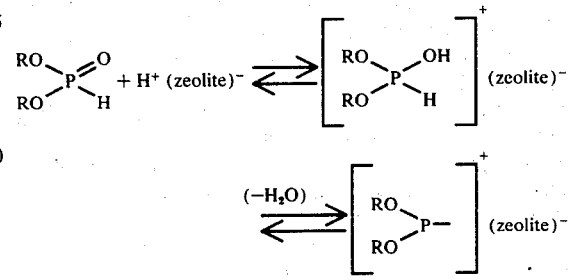

With phosphorus trichloride, it is believed that the hydrogen on the zeolite reacts with one of the $[-Cl]^-$ ions of the phosphorus trichloride to form HCl and is believed thereby to chemically bond the remainder of the phosphorus trichloride molecule, namely, the $[-PCl_2]^+$, to the crystal structure of the zeolite possibly through a silanol group. These phosphorus-containing moieties, after the heating, in the presence of free oxygen, could be present as $[PO_2]^+$ or various phosphorus anhydride or hydroxyl forms. In any case, it is believed that the phosphorus is chemically bonded to the crystal structure of the zeolite since the phosphorus-containing zeolite can be used for extended periods of time at high temperatures without loss of phosphorus. Further reference will be made to this hereinafter. Further, the phosphorus is not likely present as a crystalline framework constituent, i.e., it has not been substituted for silicon or aluminum atoms, since the unit cell dimensions of the zeolite are unchanged on incorporation of phosphorus atoms with the zeolite. Further reference to this point will also be made hereinafter.

Incorporation of the phosphorus with the zeolite provides a composition having unique properties as a catalytic agent. For example, while the zeolites as defined herein are excellent aromatization catalysts, the phosphorus-containing zeolite does not possess such aromatizing activity. The ability of the zeolite to catalyze the transformation of aliphatic hydrocarbons to aromatic hydrocarbons in commercially desirable yields is not present with the phosphorus-containing zeolite. The zeolites possess strong acid sites and, while again we do not wish to be limited to the consequences of a theory, it is believed that the strong acid sites of the zeolites are responsible for their aromatizing activity. On the other hand, the phosphorus-containing zeolite does not possess these strong acid sites. Rather, the phosphorus-containing zeolite possesses a greater number of acid sites than the parent zeolite but these sites appear to have a lesser acid strength than those found in the parent zeolite. It is believed that the apparent replacement of the strong acid sites with a greater number of relatively weak acid sites may be responsible for the unique catalytic properties of the phosphorus-containing zeolite.

Reaction of the zeolite with the phosphorus-containing compound is effected by contacting the zeolite with the phosphorus-containing compound. Where the phosphorus-containing compound is a liquid, the phosphorus-containing compound can be in solution in a solvent at the time contact with the zeolite is effected. Any solvent relatively inert with respect to the phosphorus-containing compound and the zeolite may be employed. Suitable solvents include aliphatic, aromatic or alcoholic liquids. Where the phosphorus-containing compound is trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the phosphorus-containing compound can be used by itself or can be used in admixture with a gaseous diluent relatively inert to the phosphorus-containing compound and the zeolite such as air or nitrogen.

Preferably, prior to reacting the zeolite with the phosphorus-containing compound, the zeolite is dried. Drying can be effected in the presence of air. Elevated temperatures may be eployed. However, the temperature should not be such, as mentioned hereinafter, that the crystal structure of the zeolite is destroyed.

Heating of the phosphorus-containing catalyst subsequent to preparation and prior to use is also preferred. The heating can be carried out in the presence of oxygen, for example air. Heating can be at a temperature of about 150°C. However, higher temperatures, i.e., up to about 500° C are preferred. Heating can be carried out for 3–5 hours. It has been found that heating increases the catalyst efficiency of the phosphorus-containing zeolite probably due to an increase in the number of acid sites rather than an increase in the strength of the existing acid sites. Increasing the heating temperature increases the catalyst efficiency. However, while heating temperatures above about 500° C can be employed, they are not necessary. At temperatures of about 1000° C, the crystal structure of the zeolite is destroyed.

The amount of phosphorus incorporated with the crystal structure of the phosphorus-containing zeolite should be at least about 0.78 percent by weight. With this amount of phosphorus, replacement of a sufficient proportion of the strong acid sites of the zeolite with an increased number of weak acid sites is effected. However, it is preferred in order to increase the replacement of the strong acid sites with an increased number of these weaker acid sites that the amount of phosphorus in the phosphorus-containing zeolite be at least about 2.5 percent by weight. The amount of phosphorus can be as high as about 4.5 percent by weight. The amount of phosphorus may be even higher than about 4.5 percent by weight although with these higher amounts a decline in catalytic activity can occur. By "percent by weight" we mean the unit weight of phosphorus per 100 unit weights of the zeolite. Amounts of phosphorus from about 0.78 to 4.5 percent by weight correspond to about 0.25 to 1.45 milliequivalents of phosphorus per gram of zeolite.

It was mentioned previously that the phosphorus is not likely present as a crystalline framework constituent of the phosphorus-containing zeolite. Evidence for this is set forth in Example 7 hereinafter by X-ray diffraction analysis of the zeolite before and after it has been modified by incorporation of phosphorus with the crystal structure to form the phosphorus-containing zeolite. The interplanar spacings are substantially identical for the zeolite before and after phosphorus incorporation. On the other hand, the relative intensities of the 11.10 and 9.95 A d-spacings of the phosphorus-containing zeolite are phosphorus dependent, the relative intensities decreasing with phosphorus concentration in the phosphorus-containing zeolite. The relative intensities of the remaining d-spacings are unaffected by the presence of the phosphorus in the phosphorus-containing zeolite. Characterization of the phosphorus-containing zeolite with respect to the zeolite can, in fact, be made on the basis of the decrease in the 11.10 and the 9.95 A d-spacings as a result of the incorporation of the phosphorus with the zeolite.

The amount of phosphorus incorporated with the zeolite by reaction with the phosphorus-containing compound will depend upon several factors. One of these is the reaction time, i.e., the time that the zeolite and the phosphorus-containing compound are maintained in contact with each other. With greater reaction times, all other factors being equal, a greater amount of phosphorus is incorporated with the zeolite. Another factor is the ratio of the phosphorus-containing compound to the zeolite in the reaction mixture employed to effect incorporation of the phosphorus with the zeolite. With greater ratios of phosphorus-containing compound to zeolite, again all other factors being equal, a greater amount of phosphorus is incorporated with the zeolite. Other factors upon which the amount of phosphorus incorporated with the zeolite is dependent include reaction temperature, concentration of the phosphorus-containing compound in the reaction mixture, the degree to which the zeolite has been dried prior to reaction with the phosphorus-containing compound and the conditions of drying of the phosphorus-containing zeolite after reaction of the zeolite with the phosphorus-containing compound.

It has been found that the concentration of phosphorus-induced weak acid sites, and thus the catalytic activity, of the phosphorus-containing zeolite is altered upon contact with water vapor. Thus, upon contact with water vapor the number of weak acid sites appears to be increased. This increase may occur after the phosphorus-containing zeolite is put into use as a catalyst as a result of contact with water vapor contained in the feed to the catalyst or formed during the reaction of the feed with the catalyst. Preferably, however, in order to obtain the benefits of an initial increased catalytic activity of the phosphorus-containing zeolite, the phosphorus-containing zeolite is contacted with water vapor prior to its use as a catalyst. Further, it is preferred that this contact with water vapor be carried out subsequent to contact with the phosphorus-containing compound but prior to heating. Contact of the phosphorus-containing zeolite with the water vapor may be carried out in any suitable manner. For example, sorption of water vapor of the phosphorus-containing zeolite can be effected in a vacuum desiccator at ambient conditions for one hour. Water vapor can also be sorbed by passing an inert gas such as helium through a water bubbler and passing the entrained water vapor through the phosphorus-containing zeolite in a reaction tube. Other methods of contacting the phosphorus-containing zeolite with water involve co-feeding an alcohol or ether compound during a hydrocarbon conversion catalytic reaction. These materials as well as other oxygen-containing compounds generate water in-situ during reaction and maintain the catalyst in a form active by virtue of the acid sites maintained.

As stated previously, the phosphorus-containing zeolites of this invention are effective catalysts for the conversion of aliphatic compounds, particularly hydrocarbons. The hydrocarbons may be olefinic or paraffinic. The use of the zeolite without incorporation of phosphorus for the conversion of aliphatic hydrocarbons results in the formation of appreciable quantities of aromatic compounds, as indicated previously. On the other hand, the use of the phosphorus-containing zeolite for the conversion of aliphatic hydrocarbons under substantially the same operating conditions results in the formation of only minor amounts of aromatics. With olefins, the products are mainly higher aliphatic compounds, the reaction product having high olefin to paraffin ratios. With paraffins, the products are mainly olefins and other paraffins.

Conversion of aliphatic hydrocarbons employing the phosphorus-containing zeolite as a catalyst can be carried out under a variety of reaction conditions. The temperature employed may be about 250° C to 700° C. With the more reactive aliphatic hydrocarbons, particularly olefins, temperatures in the lower portion of this range may be employed while with less reactive aliphatic hydrocarbons higher temperatures are employed. For example, effective conversion of propylene can be obtained with a temperature of about 300° C, whereas effective conversion of ethylene requires a temperature of at least about 500° C. Weight per hour space velocities may be about 1.5 to 13.5 although much higher space velocities may also be employed depending upon the activity of the aliphatic hydrocarbon reactant and the molecular weight and configuration of the product desired. Pressures may be as desired.

The phosphorus-containing zeolite may be modified by impregnating with zinc. Impregnation of the phosphorus-containing zeolite with zinc increases the activity of the phosphorus-containing zeolite for the conversion of aliphatic compounds at the lower temperatures of conversion. At temperatures above about 500° C, the effect of the zinc appears to be minimal.

The phosphorus-containing zeolite may be impregnated with the zinc by contacting the phosphorus-containing zeolite with a solution of a zinc salt. For example, the phosphorus-containing zeolite may be contacted with a sufficient amount of a solution of a zinc salt to fill the pore volume of the phosphorus-containing zeolite, the concentration of the zinc salt in the solution being such that the phosphorus-containing zeolite, when its pore volume is filled with the solution, will be impregnated with the desired amount of zinc. If the zinc salt is not sufficiently soluble in the solvent such that the desired amount of zinc will be impregnated in the phosphorus-containing zeolite, the process may be repeated one or more times after removal of the solvent by drying following each contact with the solution. The solvent for the zinc salt is preferably water. However, any relatively inert solvent may be employed.

The zinc salt may be an organic salt or an inorganic salt. Organic salts of zinc that may be employed include the acetate, benzoate, butyrate, formate, lactate, and others. Inorganic salts of zinc that may be employed include the bromide, chlorate, chloride, iodide, nitrate, sulfate, and others.

Following impregnation with the zinc salt, the phosphorus-containing zeolite is heated as described hereinabove. In this connection, where the phosphorus-containing zeolite is to be impregnated with zinc, the heating after impregnation with the zinc can substitute for the heating described hereinabove.

The amount of zinc impregnated into the phosphorus-containing zeolite may be as desired. Any finite amount will be effective. However, the amount should be at least about 1 percent by weight. On the other hand, amounts in excess of about 4 percent by weight will not ordinarily be necessary. These amounts are intended to mean the amount of zinc and do not include the anion of the salt.

With respect to the anion of the salt, heating of the phosphorus-containing zeolite following impregnation with the zinc salt or during use thereof as a catalyst removes or destroys the anion leaving the zinc as the material impregnating the phosphorus-containing zeolite.

The following examples will be illustrative of the invention.

EXAMPLE 1

This example will illustrate the preparation of phosphorus-containing zeolites.

Several preparations of crystalline aluminosilicate zeolites were combined to form a composite. Each of these aluminosilicate zeolites was ZSM-5 containing sodium as the cation associated therewith and had been prepared by conventional techniques employing tetrapropylammonium hydroxide. The composite had a silica to alumina ratio of 70 and the individual zeolite catalysts had components falling in the ranges: 1.1–1.4% Na, 4.22–7.31% C, 0.39–0.63% N, 2.25–2.45% $Al_2O_3$, and 91.3–95.0% $SiO_2$. The C/N atomic ratio was 12.5–13.5 and the Na/Al ratio was approximately 1.2.

The composite, in powder form, was brought to a temperataure of 540° C under a stream of nitrogen (the heating rate was about 2.5° C per minute) and held for 16 hours to remove residue of the tetrapropylammonium hydroxide. It was then pressed into wafers, crushed, and screened to 8–12 mesh, followed by ion exchange with 0.5 N $NH_4NO_3$, the $NH_4^+$ replacing the $Na^+$. The resulting pellets were air-dried and calcined in air at 500° C for 3–16 hours whereby $H^+$ replaced the $NH_4^+$. The sample at this point can be referred to as the "activated acid form of the zeolite."

A ten-gram sample of the zeolite was added to 3.94 cubic centimeters of trimethylphosphite dissolved in 50 cubic centimeters of n-octane in a flask. Under a slow stream of nitrogen the mixture was heated to reflux temperature (about 120° C) for 72 hours. A ten-inch vigreaux column was added to the flask for distillation and 21 grams of liquid were collected at 90°–113° C for subsequent analysis. The solids were filtered and washed with 100 cubic centimeters each of pentane, methylene chloride, and pentane. They were then air-dried followed by drying in a vacuum oven overnight at 110° C. They were next pressed into wafers, broken and screened to 8–12 mesh size and heated in air at 500° C for 3 hours. The resulting product was the phosphorus-containing zeolite.

The above procedure was repeated with ten other samples with variations in the ratio of trimethylphosphite to zeolite and reaction time, i.e., time of contact of the trimethylphosphite with the zeolite. One of the samples was heated at 300° C rather than at 500° C. Another one of the samples was treated with a large excess of neat trimethylphosphite, i.e, without any n-hexane solvent.

A portion of each of the phosphorus-containing zeolites was analyzed by X-ray. The results are listed in Table I in weight percent and are calculated on a dry weight basis after a heating of about 0.5 hour at 1000°–1100° C. This heating was only for analytical purposes of assuring dryness and whereas the phosphorus was retained the crystalline structure was probably destroyed. For comparison purposes, there is included an analysis of the zeolite, identified in the table as Sample 1, prior to conversion to a phosphorus-containing zeolite. Sample 6 was the sample heated at 300° C. Sample 11 was the sample treated with a large excess of neat trimethylphosphite. The weight loss is the thermal gravimetric weight loss and was determined at 900° C by standard techniques using a basic DuPont Model instrument. Most of the weight loss indicated in the table was found to be due to water although traces of organic material (~0.5–2 percent) were also noted in effluent gases.

TABLE I

| Sample | % P | % Al$_2$O$_3$ | % SiO$_2$ | Reaction Time, Hrs | Weight Loss |
|---|---|---|---|---|---|
| 1 | 0 | 2.20 | 94.9 | — | 3.0 |
| 2 | 4.51 | 2.03 | 89.5 | 72 | 8.0 |
| 3 | 4.42 | 2.21 | 93.1 | 66 | 8.7 |
| 4 | 3.72 | 2.03 | 91.8 | 16 | 8.0 |
| 5 | 3.21 | 2.00 | 94.2 | 17 | 7.0 |
| 6 | 3.30 | 1.94 | 92.1 | 17 | 3.4 |
| 7 | 3.77 | 1.96 | 93.2 | 16 | — |
| 8 | 4.08 | 1.85 | 91.0 | 16 | 2.7 |
| 9 | 0.78 | 2.22 | 94.4 | 16 | 6.5 |
| 10 | 1.45 | 2.08 | 95.7 | 16 | 4.5 |
| 11 | 2.68 | 1.91 | 88.7 | 16 | ~1 |

EXAMPLE 2

This example will further illustrate the preparation of a phosphorus-containing zeolite.

Six grams of activated acid form of ZSM-5 zeolite were placed in a flask fitted with a thermometer, a nitrogen purge, a reflux condenser, a dropping funnel, and a calcium chloride trap on the nitrogen exit line leading from the top of the flask. The zeolite was heated to 230°–240° C for about 2 hours while nitrogen was passed through the flask to remove moisture. After allowing the zeolite to cool, 50 cubic centimeters of phosphorus trichloride from the dropping funnel were added to the zeolite. The surface of the zeolite turned a light yellow-orange color immediately. The slurry of zeolite and phosphorus trichloride was carefully refluxed for 20 hours.

After cooling, the phosphorus-containing zeolite was filtered off, washed with 150 cubic centimeters of chloroform, and dried in a vacuum oven at 110° C. It was then placed in a quartz tube with a thermowell in the center and heated to 130°–140° C. Nitrogen saturated with water at 30°–50° C was passed through the tube for 20 hours. Hydrogen chloride was evolved in the process.

The phosphorus-containing zeolite was then heated at 150° C in dry nitrogen. Analysis of this zeolite indicated that it contained 2.95 percent by weight of phosphorus.

EXAMPLE 3

This example will still further illustrate the preparation of a phosphorus-containing zeolite.

Seven grams of activated acid form of ZSM-5 zeolite were placed in a quartz tube fitted with a thermowell in the center. The zeolite was heated in dry nitrogen at 500° C for 1.5 hours to remove moisture. After cooling to 300° C, 44 grams of phosphorus trichloride vapor were passed through the zeolite over a period of 3 hours. Nitrogen was used as a carrying gas. The system was carefully protected from moisture.

After this treatment, air was substituted for the nitrogen and was passed over the zeolite at a rate of 100 cubic centimeters per minute for 16 hours and at a temperature of 400° C. Analysis of the resulting phosphorus-containing zeolite indicated that it contained 1.38 percent by weight of phosphorus.

EXAMPLE 4

This example will illustrate still another method of preparing a phosphorus-containing zeolite.

In an apparatus similar to that described in Example 2, 15.0 grams of dry activated acid form of ZSM-5 zeolite were refluxed with 100 cubic centimeters of neat trimethylphosphite for 20 hours. After cooling, the zeolite was filtered off, washed with methylene chloride followed by pentane, pumped down in a vacuum oven, and heated in air at 500° C for 22 hours. The total dry weight after heating was 15.8 grams. Analysis of the phosphorus-containing zeolite indicated that it contained 2.68 percent by weight of phosphorus.

EXAMPLE 5

This example will illustrate another method of preparing a phosphorus-containing zeolite.

In a manner similar to that described in Example 3, 8.8 grams of activated acid form of ZSM-11 zeolite were treated with 74 grams of an equivolume solution of phosphorus trichloride and cyclohexane at 300°–450° C over a period of 3.3 hours.

EXAMPLE 6

This example will illustrate the stability of the phosphorus-containing zeolite under conditions of use as a catalyst.

The phosphorus-containing zeolites identified in Example 1 as Samples 4, 5, and 7 were each used as catalysts for conversion reactions. The conversion in which Sample 7 was employed was carried out in the presence of water vapor. In the reaction in which Sample 4 was employed, the phosphorus-containing zeolite was regenerated two times during the reaction by calcining in air at 500° C. In the reactions in which Samples 5 and 7 were employed, the phosphorus-containing zeolites were similarly regenerated one time and four times, respectively.

Analyses of the phosphorus-containing zeolites were made by X-ray prior and subsequent to being used as the catalysts and the results are given in Table II.

amount of the phosphorus. The d-spacings of the zeolite without phosphorus and the phosphorus-containing zeolite being essentially identical are indicative that the

TABLE II

| Sample No. | % P Fresh | % P Used | % $Al_2O_3$ Fresh | % $Al_2O_3$ Used | % $SiO_2$ Fresh | % $SiO_2$ Used | Reaction Time | Conditions Temperature |
|---|---|---|---|---|---|---|---|---|
| 4 | 3.72 | 3.67 | 2.03 | 2.02 | 91.8 | 87.4 | 14 hrs | 250–400°C |
| 5 | 3.30 | 3.53 | 1.94 | 1.99 | 92.1 | 88.7 | 6 hrs | 250–500°C |
| 6 | 3.77 | 3.64 | 1.96 | 1.90 | 93.2 | 97.4 | 23 hrs | 350–500°C |

It will be observed from Table II that the compositions of the phosphorus-containing zeolites were substantially unaltered, particularly as to phosphorus content, by use as a catalyst and by regeneration. The absence of loss of phosphorus indicates a strong bonding of the phosphorus with the zeolite.

phosphorus is not present as a constituent of the crystalline framework of the phosphorus-containing zeolite. It will be further observed that, with an amount of phosphorus of 0.78 percent by weight, the decrease in the 11.10 and 9.95A d-spacings was at least 15 percent.

TABLE III

| dobs A° | Wt % Phosphorus → 0 | 0.78 | 1.45 | 3.93 | 4.15 |
|---|---|---|---|---|---|
| 11.100 | 87 | 71 | 63 | 35 | 28 |
| 9.950 | 58 | 48 | 42 | 20 | 22 |
| 3.837 | 100 | 100 | 100 | 100 | 100 |
| 3.808 | 68 | 73 | 72 | 69 | 66 |
| 3.742 | 37 | 41 | 42 | 39 | 40 |
| 3.708 | 49 | 53 | 51 | 53 | 50 |
| 3.639 | 28 | 30 | 29 | 25 | 27 |

Relative Intensity, 100 I/I

EXAMPLE 7

This example will demonstrate the lack of effect of the incorporation of the phosphorus with the zeolite on the unit cell dimensions of the zeolite and the decrease in the relative intensities of the 11.10 and 9.95 A d-spacings by the incorporation of the phosphorus with the zeolite.

One ZSM-5 zeolite without phosphorus and four phosphorus-containing ZSM-5 zeolites, each of the phosphorus-containing zeolites containing a different amount of phosphorus, were subjected to X-ray analysis to determine their definitive X-ray diffraction patterns. The patterns were measured automatically by a proportional counter diffractometer using CuKα (doublet) radiation. Peak height, I, and band position as a function of 2θ were used to calculate relative intensities (100 I/I), where I is the strongest line intensity and (dobs) the interplanar spacings in angstroms. Table III compares the relative intensities of the seven major d-spacings as a function of phosphorus concentration.

It will be observed from Table III that the d-spacings are essentially identical for the zeolite without phosphorus and the phosphorus-containing zeolite. It will also be observed that there was a decrease in the relative intensities of the interplanar spacings at $d$=11.10A and $d$=9.95A of the phosphorus-containing zeolite and the decrease was in a linear manner proportional to the

EXAMPLE 8

This example will illustrate the catalytic effect of the phosphorus-containing zeolite on the conversion of an olefin, namely, ethylene.

The catalyst employed was the phosphorus-containing zeolite identified as Sample 3 in Example 1. The ethylene was passed over the catalyst at 500° C and at a weight per hour space velocity (WHSV) of 1.45. The products were collected over a one hour period and the products analyzed. For comparison purposes, ethylene was also passed at 500° C and a WHSV of 1.5 over the zeolite without phosphorus identified as Sample 1 in Example 1.

The results are given in Tables IV and V.

Table IV gives the results in terms of weight percent product selectivity and Table V gives the results in terms of weight percent product analysis.

It will be observed from Table IV that aromatics selectivity was 4.04 percent with the phosphorus-containing zeolite as compared to 37.37 percent with the zeolite without phosphorus. It will also be observed that the olefin-paraffin ratio was 38.7/1 with the phosphorus-containing zeolite as compared to 0.2/1 with the zeolite without phosphorus. It will further be observed from the table that, with the phosphorus-containing zeolite, the ethylene was converted into propylene (42.13 percent selectivity) and $C_5$'s (33.83 percent selectivity) as the major products.

TABLE IV

| CATALYST Products - Wt. % | Phosphorus-Containing Zeolite | Zeolite Without Phosphorus | | |
|---|---|---|---|---|
| $C_1$ | 3.19 | 1.17 | | |
| $C_2^=$ | — | — | OLEFIN/PARAFFIN RATIO | |
| $C_2°$ | 4.04 | 3.56 | Phosphorus-Containing Zeolite | Zeolite Without Phosphorus |
| $C_3^=$ | 42.13 | 4.11 | 38.7/1 | 0.2/1 |
| $C_3°$ | 1.28 | 25.88 | | |

TABLE IV-continued

| CATALYST<br>Products - Wt. % | Phosphorus-Containing<br>Zeolite | Zeolite<br>Without Phosphorus | | |
|---|---|---|---|---|
| $C_4H_6$ | 2.56 ⎫ | 4.96 ⎫ | | |
| $C_4°$ | 1.27 ⎭ → | 13.74 ⎭ → | 2.2/1 | 0.4/1 |
| $C_5$ | 33.83 | 4.97 | | |
| $C_6$ | 7.23 | 0.46 | | |
| $C_7^+$ | 2.34 | 0.85 | | |
| Aromatics | 4.04 | 37.37 | | |
| Conversion, Wt. % | 9.53 | 97.53 | | |
| Material Balance, Wt. % | 97.99 | 98.59 | | |

TABLE V

| CATALYST<br>Products - Wt. % | Phosphorus-Containing<br>Zeolite | Zeolite<br>Without Phosphorus |
|---|---|---|
| $H_2$ | 0 | 0.43 |
| $CH_4$ | 0.24 | 1.17 |
| $C_2H_6$ | 0.30 | 3.56 |
| $C_2H_4$ | Feed | Feed |
| $C_3H_8$ | 0.10 | 25.88 |
| $C_3H_6$ | 3.15 | 4.11 |
| $i\text{-}C_4H_{10}$ | 0.01 | 8.76 |
| $n\text{-}C_4H_{10}$ | 0.08 | 4.98 |
| $C_4H_8$ | 0.18 | 3.23 |
| $C_4H_6$ | 0.02 | 1.73 |
| $C_5$ | 2.53 | 4.97 |
| $C_6$ | 0.54 | 0.46 |
| $C_7^+$ | 0.18 | 0.85 |
| Benzene | 0.03 | 4.54 |
| Toluene | 0.04 | 14.65 |
| Xylenes | 0.10 | 12.93 |
| $C_9^+$ Aromatics | 0.14 | 5.25 |
| Conversion, Wt. % | 9.53 | 97.53 |
| Material Balance, Wt. % | 98.0 | 98.59 |

EXAMPLE 9

This example will illustrate the catalytic effect of the phosphorus-containing zeolite on the conversion of another olefin, namely, propylene.

Propylene was passed over the phosphorus-containing zeolite identified as Sample 3 in Example 1 at 300° C and 400° C. The rate of passage of the propylene was 82 cubic centimeters per minute and the amount of the phosphorus-containing zeolite was 4.75 grams. The weight per hour space velocity was 1.8. The products were collected over a one hour period at each temperature and analyzed. For comparison purposes, propylene was similarly passed over the zeolite without phosphorus identified as Sample 1 in Example 1.

The results are given in Tables VI and VII. Table VI gives the results in terms of weight percent product selectivity and Table VII gives the results in terms of weight percent product analysis.

It will be observed from the tables that the use of the phosphorus-containing zeolite as catalyst resulted in the suppression of the formation of aromatics and the production of high olefin-paraffin ratios as compared to the use of the zeolite without phosphorus. The major reaction of the propylene over the phosphorus-containing zeolite was a dimerization to $C_6$ aliphatics which are believed to be predominantly olefins. It will be observed from Table VI that, at 400° C, with the phosphorus-containing zeolite, selectivity to the $C_6$ fraction was 58 weight percent compared with about 3 weight percent using the zeolite without phosphorus. Aromatics selectivity was 3 weight percent with the phosphorus-containing zeolite with about 38 weight percent using the zeolite without phosphorus. The next major (olefinic) product fraction was $C_5$ and the combined yield based on products (selectivity) of $C_5$ and $C_6$ aliphatics from propylene was 80.9 weight percent. Associated with the very low aromatic yield was the absence of ethane and butane, and low (<1 percent) propane yield. Somewhat lower $C_6$ selectivity (39.5 percent) was obtained at 300° C. At this temperature, 300° C, compared to 400° C, the $C_5$ yield was reduced and $C_7$ increased to 21.6 weight percent. The combined $C_5$, $C_6$, and $C_7^+$ fractions totaled 74.9 weight percent.

TABLE VI

| CATALYST<br>TEMP., °C<br>Products, Wt. % | Phosphorus-<br>Containing<br>Zeolite<br>400 | Zeolite<br>Without<br>Phosphorus<br>400 | Phosphorus-<br>Containing<br>Zeolite<br>300 | Zeolite<br>Without<br>Phosphorus<br>300 |
|---|---|---|---|---|
| $CH_4$ | 0 | 0 | 0 | 0 |
| $C_2H_4$ | 0.7 | 2.1 | 1.0 | 0.1 |
| $C_2H_6$ | 0 | 0.7 | 0 | 0.1 |
| $C_3H_6$ | — | — | — | — |
| $C_3H_8$ | 0.4 | 26.8 | 0 | 8.3 |
| $C_4H_{10}$ | 0 | 17.8 | 0.6 | 10.3 |
| $C_4H_8$ | 8.8 | 1.9 | 12.8 | 3.8 |

TABLE VI-continued

| CATALYST TEMP., °C | Phosphorus-Containing Zeolite | Zeolite Without Phosphorus | Phosphorus-Containing Zeolite | Zeolite Without Phosphorus |
|---|---|---|---|---|
| Products, Wt. % | 400 | 400 | 300 | 300 |
| $C_5$ | 22.8 | 6.9 | 13.8 | 27.3 |
| $C_6$ | 58.1 | 3.4 | 39.5 | 18.5 |
| $C_7^+$ | 6.3 | 1.9 | 21.6 | 6.1 |
| Aromatics | 3.0 | 37.8 | 10.7 | 24.2 |
| Conversion, Wt.% | 15.8 | 99.4 | 10.0 | 98.6 |
| Material Balance, Wt. % | 99.6 | 102.5 | 97.0 | 100.1 |

TABLE VII

| CATALYST TEMP., °C | Phosphorus-Containing Zeolite | | Zeolite Without Phosphorus | |
|---|---|---|---|---|
| Products, Wt. % | 400 | 300 | 400 | 300 |
| $H_2$ | 0 | 0 | 0 | 0 |
| $CH_4$ | 0 | 0 | 0.03 | 0 |
| $C_2H_6$ | 0 | 0 | 0.69 | 0.06 |
| $C_2H_4$ | 0.11 | 0.09 | 2.14 | 0.11 |
| $C_3H_8$ | 0.06 | 0 | 26.79 | 8.27 |
| $C_3H_6$ | Feed | Feed | Feed | Feed |
| $i-C_4H_{10}$ | 0 | 0.02 | 12.50 | 7.86 |
| $n-C_4H_{10}$ | 0 | 0.03 | 5.37 | 2.46 |
| $C_4H_8$ | 1.38 | 1.28 | 0.15 | 1.52 |
| $C_4H_6$ | 0 | 0 | 1.75 | 2.27 |
| $C_5$ | 3.60 | 1.38 | 6.92 | 27.26 |
| $C_6$ | 9.18 | 3.96 | 3.37 | 18.49 |
| $C_7^+$ | 1.00 | 2.16 | 1.90 | 6.07 |
| Benzene | 0.08 | 0.11 | 2.07 | 0.80 |
| Toluene | 0.07 | 0.17 | 10.89 | 5.36 |
| Xylenes | 0.31 | 0.48 | 12.38 | 8.93 |
| $C_9^+$ Aromatics | 0 | 0.33 | 12.43 | 9.13 |
| Conversion, Wt. % | 15.81 | 10.04 | 99.37 | 98.58 |
| Material Balance, Wt. % | 99.6 | 97.0 | 102.50 | 100.11 |

EXAMPLE 10

This example will illustrate the catalytic effect of the phosphorus-containing zeolite at higher space velocities on the conversion of propylenes.

Propylene was passed at three different temperatures over phosphorus-containing zeolite prepared from an activated acid form of ZSM-5 zeolite at a weight per hour space velocity of 13.5. The products were collected and analyzed. Table VIII gives the temperatures of reaction, the degree of conversion, and the product selectivities.

TABLE VIII

| Temperature, °C | 300 | 350 | 400 |
|---|---|---|---|
| Conversion, Wt. % | 29.2 | 45.3 | 54.8 |
| Products, Wt. % | | | |
| Ethylene | 0.1 | 0 | 0.1 |
| Butenes | 25.4 | 30.2 | 37.9 |
| $C_5$ | 38.2 | 37.8 | 29.3 |
| $C_6$ | 14.8 | 13.9 | 17.2 |
| $C_7$ | 17.3 | 15.9 | 15.0 |
| Aromatics | 4.2 | 2.2 | 0.5 |

TABLE VIII-continued

| Temperature, °C | 300 | 350 | 400 |
|---|---|---|---|
| Conversion, Wt. % | 29.2 | 45.3 | 54.8 |
| Products, Wt. % | | | |
| Total | 100.0 | 100.0 | 100.0 |

It will be seen from the table that the major products were $C_4-C_7$ aliphatic compounds which are rich in olefins. It will also be seen from the table that the amount of butenes was relatively high. It will further be seen from the table that the $C_5-C_7$ aliphatic fraction consisted largely of mixtures of olefinic compounds.

EXAMPLE 11

This example will illustrate the catalytic activity of the phosphorus-containing zeolite on the conversion of a paraffin, namely, n-hexane.

N-hexane was passed over the phosphorus-containing zeolite identified as Sample 3 in Example 1 at 600° C and 700° C. The weight per hour space velocity was 1.96 and 1.95, respectively. The products were analyzed and the results in terms of product selectivities are set forth in Table IX. For comparison purposes, there is included in the table the results obtained by passing n-hexane over three different zeolites without phosphorus at 600° C and 700° C and at a weight per hour space velocity of 2.0. The zeolite identified in the table as A was the same as the zeolite identified as Sample 1 in Example 1. The zeolites identified in the table as B and C were similar but were smaller and larger crystallites than the zeolite identified as A. Further, in the conversion reaction employing the zeolite identified as C, air was co-fed with the n-hexane and the products included 14.8 percent by weight of carbon monoxide and carbon dioxide.

It will be observed from the table that the use of the phosphorus-containing zeolite resulted in a lower yield of aromatics as compared to the zeolite without phosphorus. It will also be observed that, in addition, the use of the phosphorus-containing zeolite resulted in a greater yield of olefins than the zeolite without phosphorus.

TABLE IX

| CATALYST TEMP., °C | Phosphorus-Containing Zeolite | Zeolite Without Phosphorus | | Phosphorus-Containing Zeolite | Zeolite Without Phosphorus | |
|---|---|---|---|---|---|---|
| | | A | B | | B | C |
| Products, Wt. % | 600 | 600 | 600 | 700 | 700 | 700 |
| $H_2$ | 0.36 | 1.5 | 1.4 | 1.24 | 3.2 | 1.4 |
| $CH_4$ | 8.74 | 14.0 | 9.8 | 24.90 | 17.9 | 13.9 |
| $C_2H_6$ | 10.76 | 17.8 | 19.3 | 14.92 | 16.9 | 9.2 |
| $C_2H_4$ | 17.68 | 7.3 | 11.8 | 33.01 | 11.5 | 21.7 |
| $C_3H_8$ | 4.94 | 11.9 | 11.5 | 2.12 | 0.6 | 1.8 |
| $C_3H_6$ | 30.89 | 4.4 | 6.2 | 17.44 | 1.6 | 9.9 |

TABLE IX-continued

| CATALYST<br>TEMP., °C<br>Products, Wt. % | Phosphorus-<br>Containing<br>Zeolite<br>600 | Zeolite Without Phosphorus | | Phosphorus-<br>Containing<br>Zeolite<br>700 | Zeolite Without Phosphorus | |
|---|---|---|---|---|---|---|
| | | A<br>600 | B<br>600 | | B<br>700 | C<br>700 |
| i-$C_4H_{10}$ | 0.04 | 0.4 | 0.4 | 0.14 | 0.2 | 0.2 |
| n-$C_4H_{10}$ | 0.60 | 0.3 | | 0.2 | | 0 |
| $C_4H_8$ | 8.13 | 0.4 | 0.3 | 0.74 | 0.1 | 0 |
| $C_4H_6$ | 0 | 0.1 | | 0.2 | | 0 |
| $C_5$ | 13.10 | 0.9 | 0.8 | 1.52 | 0.1 | 0.2 |
| $C_7^+$ | 2.27 | 0.4 | 0 | 0.16 | 0 | ~0 |
| Aromatics | 2.49 | 40.4 | 38.6 | 3.96 | 47.9 | 24.3 |
| Conversion, Wt. % | 38.81 | 100.0 | 99.8 | 82.61 | 100.0 | 99+ |

EXAMPLE 12

This example will illustrate the catalytic effect of the phosphorus-containing zeolite on the conversion of a paraffin, namely, n-hexane, in the presence of a diluent, namely, water or nitrogen.

N-hexane was passed at 600° C over phosphorus-containing zeolite containing 4.38 weight percent of phosphorus prepared from an activated acid form of ZSM-5 zeolite. In Run No. 1, the n-hexane was diluted with nitrogen and in Run No. 2 the n-hexane was diluted with water. The products were collected and analyzed. The results are given in Table X in terms of weight percent product selectivities. The table also gives the weight per hour space velocities of n-hexane and of the nitrogen and water. The weight percent conversion in Run No. 1 was 16 and in Run No. 2 was 3.9.

TABLE X

| Run No. | 1 | | 2 | |
|---|---|---|---|---|
| WHSV | N-hexane | 2.7 | N-hexane | 2.7 |
| | Nitrogen | 1.7 | Water | 1.2 |
| | Total | 4.4 | Total | 3.9 |
| Products, Wt. % | | | | |
| Methane | | 13.3 | | 11.5 |
| Ethane | | 9.2 | | 7.4 |
| Propane | | 0.6 | | 0.7 |
| Butanes | | 0 | | 0 |
| Total, $C_1$–$C_4$ paraffins | | 22.9 | | 19.6 |
| Ethylene | | 29.0 | | 26.2 |
| Propylene | | 22.5 | | 25.6 |
| Butenes | | 14.5 | | 19.9 |
| Total, $C_2$–$C_4$ olefins | | 66.0 | | 71.7 |
| $C_5$ | | 10.9 | | 8.7 |
| Total | | 100.0 | | 100.0 |

It will be noted from the table that no aromatics were detected and that the major products were $C_2$–$C_4$ olefins.

EXAMPLE 13

This example will illustrate the catalytic activity of phosphorus-containing zeolite impregnated with zinc on the conversion of a paraffin, namely, n-hexane.

A phosphorus-containing zeolite containing 4.45 percent by weight of phosphorus prepared from activated acid form of ZSM-5 zeolite was immersed in an amount of aqueous solution of zinc nitrate sufficient to fill its pore volume. Thereafter, the phosphorus-containing zeolite containing the zinc nitrate solution was heated at 500° C for one hour in a stream of air at 100 cubic centimeters per minute. The resulting zinc-impregnated, phosphorus-containing zeolite contained 1 percent by weight of zinc.

N-hexane was passed over the zinc-impregnated, phosphorus-containing zeolite at four different temperatures. The products were collected and analyzed. Table XI gives the temperatures, the weight per hour space velocities, the conversion, and the results obtained in terms of product selectivities.

TABLE XI

| Run No. | 1 | 2 | 3 | 4 |
|---|---|---|---|---|
| Temp., °C | 500 | 550 | 600 | 650 |
| WHSV | 3.1 | 3.0 | 3.0 | 3.0 |
| Conversion, Wt. % | 3.4 | 13.0 | 42.0 | 78.4 |
| Products, Wt. % | | | | |
| Hydrogen | 0 | 0.3 | 0.1 | 0.8 |
| Methane | 0 | 7.1 | 12.1 | 14.1 |
| Ethane | 0 | 10.8 | 13.8 | 12.1 |
| Propane | 23.3 | 11.2 | 5.7 | 3.9 |
| Butanes | 0 | 0.6 | 0.8 | 0.4 |
| Total $H_2$+$C_1$–$C_4$ paraffins | 23.3 | 30.0 | 32.5 | 31.3 |
| Ethylene | 0 | 14.3 | 23.0 | 24.6 |
| Propylene | 22.4 | 29.0 | 26.7 | 23.9 |
| Butenes | 0 | 5.1 | 5.8 | 3.5 |
| Total $C_2$–$C_4$ olefins | 22.4 | 48.4 | 55.5 | 52.0 |
| $C_5$ | 38.6 | 21.6 | 9.4 | 8.5 |
| $C_7^+$ | 15.7 | 0 | 1.1 | 0.9 |
| Aromatics | 0 | 0 | 1.5 | 7.3 |
| Total | 100.0 | 100.0 | 100.0 | 100.0 |

EXAMPLE 14

This example will illustrate the catalytic activity of the phosphorus-containing zeolite on the conversion of another olefin, namely, butene-2 (a mixture of cis and trans isomers).

Butene-2 was passed at four different temperatures over phosphorus-containing zeolite prepared from an activated acid form of ZSM-5 zeolite. In the first three runs, the phosphorus-containing zeolite contained 4.38 weight percent of phosphorus and the butene-2 was mixed with nitrogen. In the fourth run, the phosphorus-containing zeolite contained 3.67 weight percent of phosphorus and nitrogen was not mixed with the butene-2. The products were collected and analyzed. Table XII gives the temperatures, the weight per hour space velocities of the butene-2 and, where used, of the nitrogen, the conversion in weight percent and the product selectivities in weight percent.

TABLE XII

| Run No. | 1 | 2 | 3 | 4 |
|---|---|---|---|---|
| Temp., °C | 275 | 300 | 325 | 350 |
| Conversion, Wt. % | 24.7 | 46.0 | 52.8 | 87.3 |
| WHSV | | | | |
| Butene-2 | 2.7 | 2.7 | 2.7 | 2.4 |
| Nitrogen | 1.6 | 1.6 | 1.6 | 0 |
| Total | 4.3 | 4.3 | 4.3 | 2.4 |

TABLE XIII

| Run No.<br>Products, Wt. % | 1 | | 2 | | 3 | |
|---|---|---|---|---|---|---|
| $H_2$ | 1.01 | (1.5) | 0.74 | (1.1) | 0.54 | (0.8) |
| $CH_4$ | 11.64 | (17.0) | 11.06 | (16.2) | 10.56 | (16.1) |
| $C_2H_6$ | 8.52 | (12.4) | 7.82 | (11.4) | 8.14 | (12.4) |
| $C_2H_4$ | 13.18 | (19.2) | 13.23 | (19.4) | 12.84 | (19.5) |
| $C_3H_8$ | 2.23 | (3.3) | 1.93 | (2.8) | 2.00 | (3.0) |
| $C_3H_6$ | 15.75 | (23.0) | 17.18 | (25.2) | 17.81 | (27.1) |
| $C_4H_{10}$ | 0.89 | (1.3) | 1.03 | (1.5) | 1.00 | (1.4) |
| $C_4H_8$ | 2.81 | (4.1) | 4.00 | (5.8) | 3.39 | (5.2) |
| $C_4H_6$ | 1.37 | (2.0) | 2.17 | (3.2) | 1.57 | (2.4) |
| $C_5$ | 11.00 | — | 11.28 | — | 12.24 | — |
| $C_6$ | 10.10 | — | 10.56 | — | 11.69 | — |
| $C_7^+$ | 3.00 | — | 2.86 | — | 3.41 | — |
| Benzene | 5.41 | (7.1) | 4.63 | (5.9) | 3.93 | (5.1) |
| Toluene | 7.12 | (6.2) | 6.41 | (5.1) | 5.86 | (4.5) |
| Xylenes | 3.90 | (−1.2) | 3.44 | (−1.6) | 3.34 | (−1.7) |
| $C_9^+$ Aromatics | 2.00 | (3.0) | 0.99 | (1.4) | 1.69 | (2.6) |
| Total Aromatics | 18.43 | (14.9) | 15.47 | (10.8) | 13.82 | (10.5) |
| Conversion, Wt.% | 68.51 | | 68.30 | | 65.75 | |

TABLE XII-continued

| Products, Wt. % | | | | |
|---|---|---|---|---|
| Ethane | 0.1 | 0 | 0 | 0 |
| Propane | 0 | 0 | 0.1 | 1.3 |
| Butanes | 1.4 | 1.1 | 1.1 | 3.0 |
| Total $C_2$-$C_4$ paraffins | 1.5 | 1.1 | 1.2 | 4.3 |
| Ethylene | 0.7 | 1.9 | 0.3 | 0.4 |
| Propylene | 7.8 | 13.1 | 18.4 | 1.5 |
| $C_4H_8$ | — | — | — | 3.5 |
| Total $C_2$-$C_4$ olefins | 8.5 | 15.0 | 18.7 | 5.4 |
| $C_5$ | 30.8 | 28.9 | 39.2 | 40.7 |
| $C_6$ | 11.1 | 15.8 | 15.5 | 28.7 |
| $C_7^+$ | 40.0 | 32.5 | 24.1 | 10.8 |
| Aromatics | 8.1 | 6.7 | 1.3 | 10.1 |
| Total | 100.0 | 100.0 | 100.0 | 100.0 |

It will be observed from the table that the major products were $C_5^+$ compounds. These compounds are highly olefinic in nature and are mixtures of isomers. The amounts of aromatic compounds are relatively small.

EXAMPLE 15

This example will illustrate the catalytic activity of the phosphorus-containing zeolite on the conversion of a predominantly paraffinic feed, namely, a light naphtha.

An Arabian light naphtha ($C_5$-290° F, density=0.6984) was fed at 650° C over a phosphorus-containing zeolite prepared from an activated acid form ZSM-5. The naphtha had a composition in weight percent as follows: $C_5$-19.51, $C_6$-47.80, $C_7^+$-24.06, benzene-0.57, toluene-2.90, xylene-5.07, $C_9^+$ aromatics-0, and total aromatics-8.54. The phosphorus-containing zeolite contained 4.42 weight percent of phosphorus and was calcined in air at 500° C prior to making three two-hour runs at WHSV's of 2.41, 2.38, and 2.44, respectively. The products were collected and analyzed. Table XIII gives the conversion and the products in weight percent. In the table, the figures in parentheses are the product selectivities in weight percent.

It will be observed from the table that the results are roughly comparable to those obtained with the n-hexane in Example 11. The $C_2$-$C_4$ olefins were formed in 51 weight percent selectivity (average of the three runs) at 650° C compared with 56 weight percent selectivity from n-hexane at 600° C and 700° C. Aromatics were slightly higher than with n-hexane, averaging 7.9 percent new aromatics formed. The feed naphtha, as indicated, contained 8.54 weight percent of aromatics.

We claim:
1. A composition of matter comprising a crystalline aluminosilicate zeolite containing hydrogen ions, having a silica to alumina ratio of at least about 12, a constraint index of about 1 to 12, said zeolite having been contacted with a phosphorus compound to combine therewith at least about 0.78 percent by weight of phosphorus.

2. The composition of claim 1 wherein the amount of phosphorus is about 0.78 to 4.5 percent by weight.

3. The composition of claim 1 wherein the amount of phosphorus is at least about 2.5 percent by weight.

4. The composition of claim 1 wherein the silica to alumina ratio is at least about 30.

5. The composition of claim 1 wherein said zeolite is ZSM-5.

6. The composition of claim 1 wherein said zeolite is ZSM-11.

7. The composition of claim 1 wherein said zeolite is ZSM-12.

8. The composition of claim 1 wherein said zeolite is ZSM-21.

9. The composition of claim 1 wherein said zeolite is TEA mordenite.

10. The composition of claim 1 wherein said zeolite has a dried crystal density of not less than about 1.6 grams per cubic centimeter.

11. The composition of claim 1 impregnated with zinc.

12. The composition of claim 11 wherein the amount of zinc is at least about 1 percent by weight.

13. The composition of claim 12 wherein the amount of zinc is about 1 to 4 percent by weight.

14. The process for preparing a phosphorus-containing zeolite which comprises contacting a zeolite containing hydrogen ions with a phosphorus-containing compound and thereafter heating, wherein said zeolite containing hydrogen ions is a crystalline aluminosilicate zeolite having a silica to alumina ratio of at least about 12 and a constraint index of about 1 to 12.

15. The process of claim 14 wherein said zeolite is ZSM-5.

16. The process of claim 14 wherein said zeolite is ZSM-11.

17. The process of claim 14 wherein said zeolite is ZSM-12.

18. The process of claim 14 wherein said zeolite is ZSM-21.

19. The process of claim 14 wherein said zeolite is TEA mordenite.

20. The process of claim 14 wherein said zeolite has a dried crystal density of not less than about 1.6 grams per cubic centimeter.

21. The process of claim 14 wherein said phosphorus-containing compound is trimethylphosphite.

22. The process of claim 14 wherein said phosphorus-containing compound is phosphorus trichloride.

23. The process of claim 14 wherein said phosphorus-containing compound is in solution in a solvent.

24. The process of claim 14 wherein said solvent is n-hexane.

25. The process of claim 14 wherein said heating is effected at temperatures of about 150° C to 500° C.

26. The process of claim 14 wherein said heating is effected in the presence of oxygen.

27. The process of claim 14 wherein said zeolite is contacted with water vapor subsequent to contact with said phosphorus-containing compound and prior to heating.

28. The process of claim 14 wherein, subsequent to contacting said zeolite with said phosphorus-containing compound, said zeolite is impregnated with zinc.

29. The process of claim 14 wherein said zeolite is impregnated with said zinc by contacting with a solution of a zinc salt.

30. The process of claim 29 wherein said zinc salt is an organic salt.

31. The process of claim 29 wherein said zinc salt is an inorganic salt.

32. The process of claim 31 wherein said zinc salt is zinc nitrate.

\* \* \* \* \*

UNITED STATES PATENT AND TRADEMARK OFFICE
CERTIFICATE OF CORRECTION

PATENT NO. : 3,972,832
DATED : August 3, 1976
INVENTOR(S) : STEPHEN A. BUTTER and WARREN W. KAEDING It is certified that error appears in the above-identified patent and that said Letters Patent are hereby corrected as shown below:

Column 1, line 17, "Mobile" should be --Mobil--.

Column 3, line 68, after 500°C. "solution air" should read --in air--.

Column 9, line 4, "of" should be --on--.

Signed and Sealed this

Eighth Day of March 1977

[SEAL]

Attest:

RUTH C. MASON
Attesting Officer

C. MARSHALL DANN
Commissioner of Patents and Trademarks